(12) United States Patent
Biedermann et al.

(10) Patent No.: US 7,195,632 B2
(45) Date of Patent: Mar. 27, 2007

(54) CONNECTING ELEMENT

(75) Inventors: Lutz Biedermann, VS-Villingen (DE); Peter Ostermann, Bocholt (DE)

(73) Assignee: Biedermann Motech GmbH (DE)

( * ) Notice: Subject to any disclaimer, the term of this patent is extended or adjusted under 35 U.S.C. 154(b) by 418 days.

(21) Appl. No.: 10/470,255

(22) PCT Filed: Jul. 22, 2002

(86) PCT No.: PCT/EP02/08165

§ 371 (c)(1),
(2), (4) Date: Jul. 23, 2003

(87) PCT Pub. No.: WO03/011156

PCT Pub. Date: Feb. 13, 2003

(65) Prior Publication Data

US 2004/0059330 A1   Mar. 25, 2004

(30) Foreign Application Priority Data

Jul. 25, 2001   (DE) ............................... 101 36 162

(51) Int. Cl.
*A61B 17/56* (2006.01)
*A61F 5/04* (2006.01)

(52) U.S. Cl. .......................................... 606/61; 606/59

(58) Field of Classification Search ................ 606/61, 606/72, 60, 63, 54, 71, 59
See application file for complete search history.

(56) References Cited

U.S. PATENT DOCUMENTS

| | | | |
|---|---|---|---|
| 5,092,867 A | 3/1992 | Harms et al. | |
| 5,312,405 A * | 5/1994 | Korotko et al. | 606/61 |
| 5,672,176 A * | 9/1997 | Biedermann et al. | 606/61 |
| 5,752,955 A * | 5/1998 | Errico | 606/61 |
| 5,947,966 A * | 9/1999 | Drewry et al. | 606/61 |
| 6,602,253 B2 | 8/2003 | Richelsoph et al. | |
| 6,676,661 B1 * | 1/2004 | Martin Benlloch et al. | 606/61 |
| 6,875,211 B2 * | 4/2005 | Nichols et al. | 606/61 |
| 6,887,241 B1 * | 5/2005 | McBride et al. | 606/61 |

FOREIGN PATENT DOCUMENTS

| | | |
|---|---|---|
| DE | 38 23 737 C2 | 5/1990 |
| EP | 0 578 320 A1 | 1/1994 |
| EP | 0 732 081 A1 | 9/1996 |
| EP | 0 953 316 A1 | 11/1999 |
| FR | 964 924 | 2/1950 |
| WO | WO 91/16020 | 10/1991 |
| WO | WO 00/57801 | 10/2000 |
| WO | WO 02/30307 A2 | 4/2002 |
| WO | WO 02/064016 A2 | 8/2002 |

* cited by examiner

*Primary Examiner*—Pedro Philogene
(74) *Attorney, Agent, or Firm*—Christie, Parker & Hale, LLP.

(57) ABSTRACT

A connecting element is created for connecting two rods (6, 9) or screws used for bone or vertebra stabilisation. The connecting element has a connecting part (10), a first part connectable to one of the rods and a second part connectable to the other rod. The connecting part is adjustable in length in the direction of the connecting axis of the first part and the second part and can therefore be adapted to different rod distances.

8 Claims, 2 Drawing Sheets

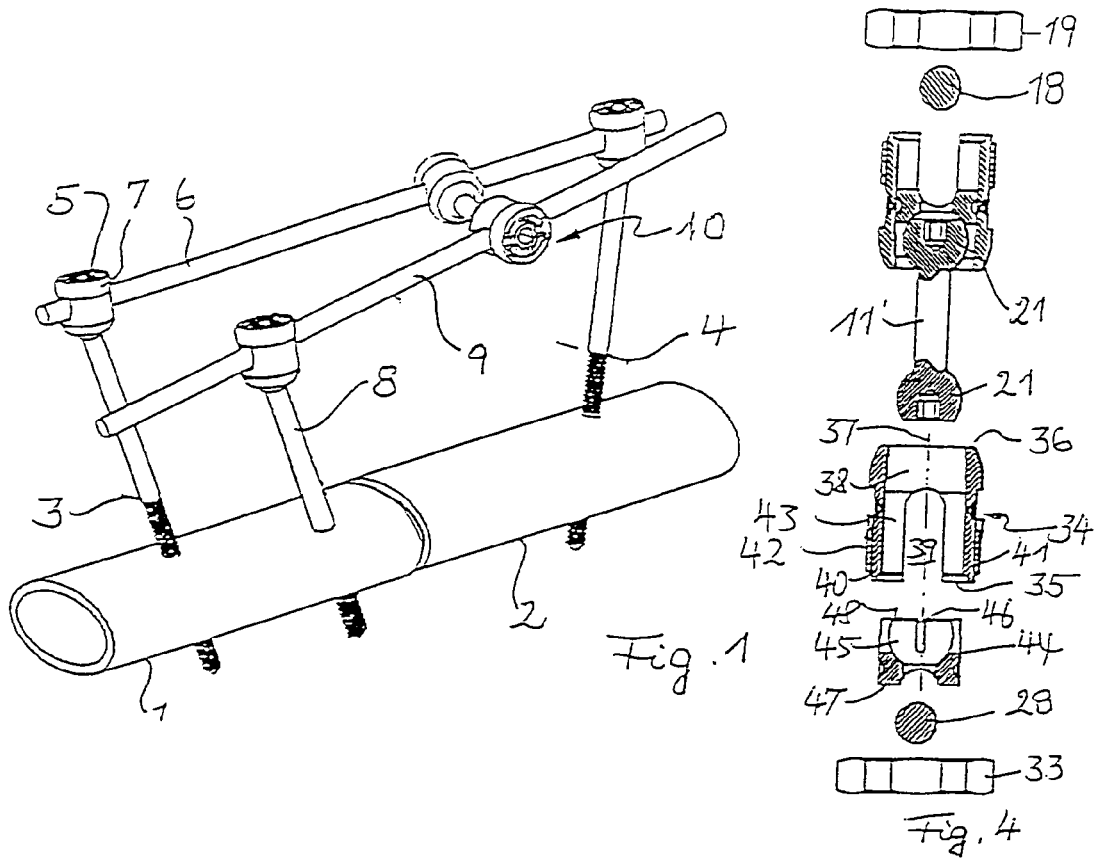
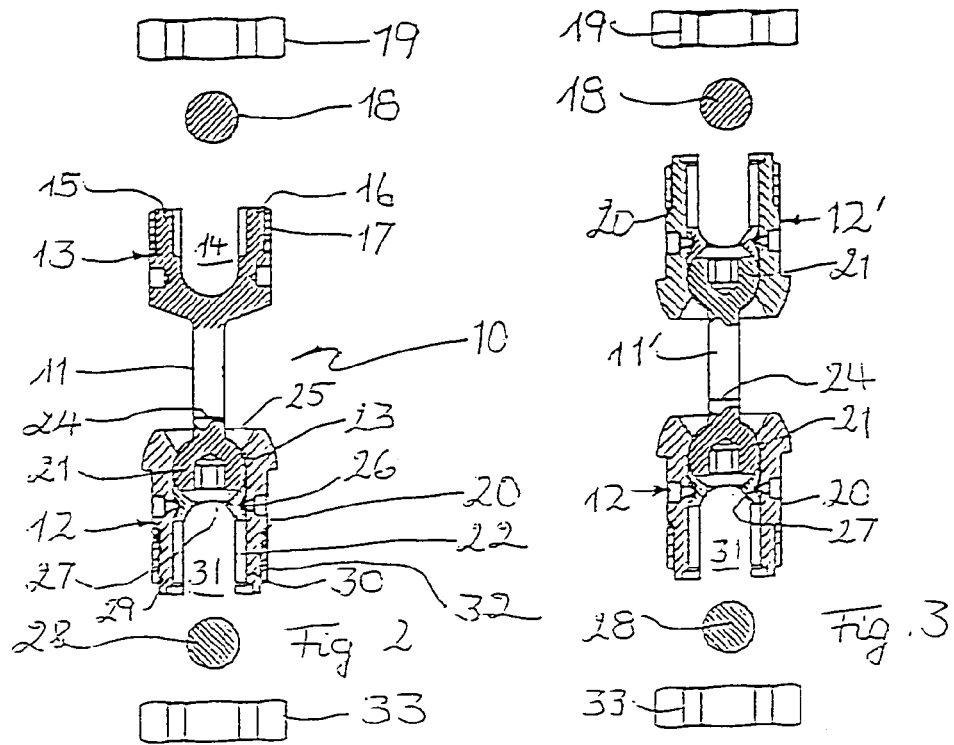

US 7,195,632 B2

CONNECTING ELEMENT

The invention relates to a connecting element for connecting two rod-shaped elements used for bone or vertebra stabilisation with a connecting part, a first part connectable to one of the rod-shaped elements and a second part connectable to the other rod-shaped element.

BACKGROUND

A connecting part is known from WO 91/16020. The connecting part has two channels, constructed in the shape of cylindrical sections, which serve to receive two rods parallel to one another. Connection of rods inclined towards one another or running diagonally to one another is not possible with this.

Furthermore, a connecting part of this kind can be used only for a predetermined distance between the rods.

SUMMARY

The object of the invention is to create a connecting element which allows adaptation to the distance between the rods to be connected.

A connecting element of this kind has the great advantage that the length of the connecting element can be adjusted during the operation.

Further developments of the connecting element include the additional advantage that the surgeon has freedom in aligning the rods as a function of the desired alignment of the parts to be connected.

BRIEF DESCRIPTION OF THE DRAWINGS

Further features and advantages of the invention emerge from the description of embodiment examples using the figures.

FIG. 1 shows a perspective illustration of a case of application.

FIG. 2 shows a sectional illustration through a first embodiment of a connecting element.

FIG. 3 shows a sectional illustration through a second embodiment of a connecting element.

FIG. 4 shows a sectional illustration through a modified embodiment.

DETAILED DESCRIPTION

Figure 5:
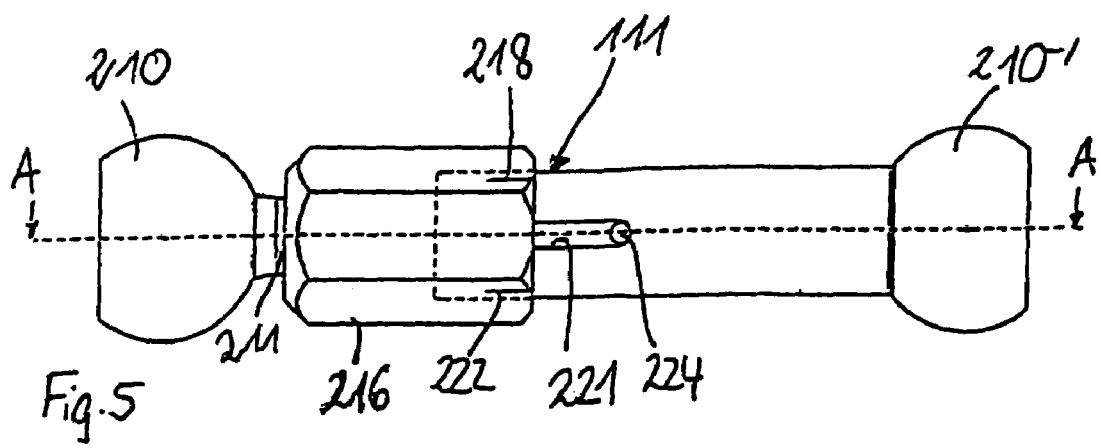
FIG. 5 shows a horizontal projection on to the connecting part according to the invention of the connecting element according to a further embodiment.

In FIG. 1 two tubular bone parts 1,2 to be connected to one another and fixed in respect of one another are shown. A screw 3, 4, known from vertebral column surgery as a pedicle screw, is screwed into each of the two parts. Each of the screws has a head 5 with a receiving orifice for receiving a rod 6. The rod is rigidly connected to the head with the aid of a nut 7. As can be seen from FIG. 1, a third screw 8, constructed exactly like the first two screws and receiving a second rod 9 in its head, is screwed into the part 1.

The second rod 9 is connected to the first rod 6 via a connecting element 10. This provides additional stabilisation.

In the above embodiment example the two parts 1 and 2 to be connected are tubular bone parts. In the same way application of at least two rods with corresponding screws for receiving thereof takes place in vertebral column surgery, possibly with an internal fixator, as known, for example, from DE 38 23 737-C.

In the embodiment shown in FIG. 2 the connecting element 10 has a shank 11 with a first part 12 on one of its ends and a second part 13 on its other end.

The second part 13 comprises two legs 15, 16, limiting a U-shaped channel 14. The two legs 15, 16 have a cylindrical shape externally and have an outer thread 17 on their open ends. The U-shaped channel 14 has a diameter which is substantially identical to or slightly larger than the diameter of a rod 18 to be received and is chosen as just large enough for the rod 18 to be inserted into the U-shaped channel 14 and to be guided thereby in the lateral direction. Further provided is a nut 19, which is equipped with its inner thread in such a way that it cooperates with the outer thread 17. The thread 17 is constructed in such a way that the distance from the thread to the floor of the U-shaped channel 14 is smaller than the diameter of the rod 18, so the rod 18 placed in the U-shaped channel 14 can be fixed by screwing down the nut 19.

As can be seen from FIG. 2, the other end of the shank 11 has a head 21 comprising a spherical section. The first part 12 has a cylindrically constructed mount 20, the diameter of which is substantially identical to or slightly larger than the diameter of the head 21 and is dimensioned in such a way that the head can be inserted into the bore and guided thereby.

In the embodiment example shown the bore 22 has a floor 23 which is spherically constructed, its radius being identical to the radius of the head 21. As can be seen from FIGS. 2 and 3, the shank 11 is constructed as separable from the spherical head via a screw connection.

One of the two parts has a threaded bore while the other part has a screw part which can be screwed into the threaded bore. This connection is schematically indicated by the connecting point 24. The threaded bore can also be provided directly in the head 21 and the shank 11 then has on its end facing the head a correspondingly constructed screw projection which can be brought into engagement with the threaded bore to screw together the two parts.

In the embodiment shown in FIG. 2 firstly the shank 11 is unscrewed from the head 21, so the head 21 can be inserted therein from the open end of the bore 22 into the position shown. The shank 11 is then screwed on, so the connection shown in the figure is produced.

As FIG. 2 further makes clear, adjacent to the floor 23 is a second bore 25, which is widened in a funnel shape, so the shank 11 can be swivelled about a solid angle relative to the mount 20.

After the head 21 has been inserted, a pressure element 26, which is constructed as spherical on its side facing the head, with a radius corresponding to the radius of the head 21, is placed into the bore 22. On its side facing away from the head 21 the pressure element has a cylindrical surface 27 in which the diameter of this cylinder is identical to the diameter of the rod 28 to be received, so the rod 28 can be placed into the recess 27. As can be seen from FIG. 2, the recess is further constructed in such a way that a U-shaped channel 31, coaxial to the bore 22, is formed with legs 29, 30 limiting the channel. The two legs 29, 30, like the second part 13, have adjacent to their open ends an outer thread 32, which extends to the other end of the mount 20 to such an extent that its distance from the floor of the cylindrical recess is smaller than the diameter of the rod 28. Further provided is a nut 33, the inner thread of which corresponds to the outer thread 32.

In operation first the rod 18 is inserted into the monoaxially acting second part 13 or into its U-shaped channel 14. Then the rod is fixed with the aid of the nut 19. The mount 20 is subsequently aligned in such a way that it receives the second rod 28 into itself. After the rod 18 has been inserted, the nut 33 is screwed down. This not only fixes the rod 18, but also exerts via the rod 28 and the pressure element 26 a pressure on the head 21 such that it is stabilised in its axial position.

In the embodiment shown in FIG. 3 the mount 20, the pressure element 26, the head 21, the rod 28 and the nut 33 coincide in all details with the first part 12 in FIG. 2. The embodiment differs only in that the second part is formed not as a monoaxial connection but also as a polyaxial connection. This second part 12' is constructed as mirror symmetrical to the first part 12. All parts of mount, head, pressure element, rod and nut coincide with the corresponding parts of the first part 12. For assembly, as in the previously described embodiment example, the shank 11 is detachable by means of a screw connection along line 24. After the heads 21 have been inserted the two parts of the shank 11 are rigidly connected to one another.

In operation the connection takes place as previously described using the first part 12, wherein the mount is orientated in each case towards the rod to be received before fixing and the rod is then placed in and fixed via the nut. By exerting the pressure from the nut via the rod and the pressure element the head is then also finally fixed.

In a modified embodiment, not shown, the mount 20 or the second part 13 can have in each case, adjacent to its open end, another inner thread into which an inner screw can be screwed, in order in this way to achieve blocking of the screw connection in a manner known per se.

In the above-described embodiments the head 21 is inserted in each case from the open end of the U-shaped recess. In a modified embodiment the bore 22 can extend through the entire mount. The head is then inserted from the end of the bore 22 facing away from the legs and held in the bore by a detent ring or snap ring to be attached. It is decisive that the open edge which surrounds the head on the end facing the shank 11 is widened in the shape of a cone, in order to enable a polyaxial movement between mount and head or shank.

The embodiment shown in FIG. 4 coincides completely in respect of shank 11', head 21, rod 18 or 28 and nut 19 or 33 with the embodiment described in FIG. 3. The mount 34 is differently constructed. It has a first end 35 and a second end 36 opposite this. A bore 38 coaxial to the symmetrical axis 37 of the mount is provided. A U-shaped recess 39 is further present, issuing from the first end 35 and extending crosswise to the symmetrical axis 39. The U-shaped recess is limited by two legs 40, 41. Adjacent to the first end 35 the two legs 40, 41 have an outer thread 42. The diameter of the U-shaped recess 39 is identical to or slightly larger than the diameter of the rod 18 or 28 and just large enough for the rod to be inserted into the recess and guided laterally by the sides of the U-shaped recess. The outer thread 42 is constructed, as with the previously described embodiments, at a distance from the floor of the U-shaped recess such that the space between it and the U-shaped floor is smaller than the diameter of the rod to be received. Further provided, as in the previously described embodiment example, is a nut 33 which cooperates with the outer thread 42.

Differing from the previously described embodiment examples, the cylindrical section 43 of the coaxial bore extends to a predetermined distance from the second end 36 and from there onwards is conically tapered towards the second end 36 at a conical angle. A pressure element 44 is further provided, the outer face of which is constructed conically towards the second end 36 in a region 45 laterally encircling the head 21, wherein the conical angle corresponds to that of the conical region of the bore. The conical region has a slit 46 directed towards the second end 36 and running open towards this end. By adapting the conical faces between bore 38 and pressure element 44, in the fully inserted state self-catching follows. The pressure element has in the way known from EP 0 732 081 B a first end 47 and a second end 48 opposite this. Adjacent to the first end is provided a substantially cylindrical section, the outer diameter of which is chosen in such a way that the pressure element can slide in the cylindrical section 43. As can be seen from the figure, the pressure element has in its second region a recess, shaped like a spherical segment and open to the second end, for receiving the screw head. Otherwise the mount 34 and the pressure element 44 coincide with the disclosure in the mentioned EP 0 732 081, which is herewith made part of the description.

The device shown in FIG. 4 is constructed as mirror symmetrical, so the other end of the shank 11' with its head, the mount and the pressure element is constructed as identical to that previously described.

In operation the pressure element is inserted into the mount 34 from the first end 35. The head 21 is inserted or pressed into the region 45 from the second end 36. The rod 28 is then placed into the remaining U-shaped slot and via the screwing down of the outer nut 33 pressure is exerted on the rod 28 and via this on the pressure element 44 encircling the head 21 in such a way that rod 28 and spherical head 21 are fixed. The process is carried out correspondingly on the opposite side.

This version also allows swivelling of the shank 11' about a predetermined framing angle and the symmetrical axis 37, so alignment or adaptation to the rods or rods with screws to be connected becomes possible.

Alternatively, the device can also be constructed in such a way that a head with mount is constructed in the manner shown in FIG. 4 and the other head is formed in the monoaxial manner described in FIG. 2.

Figure 6:
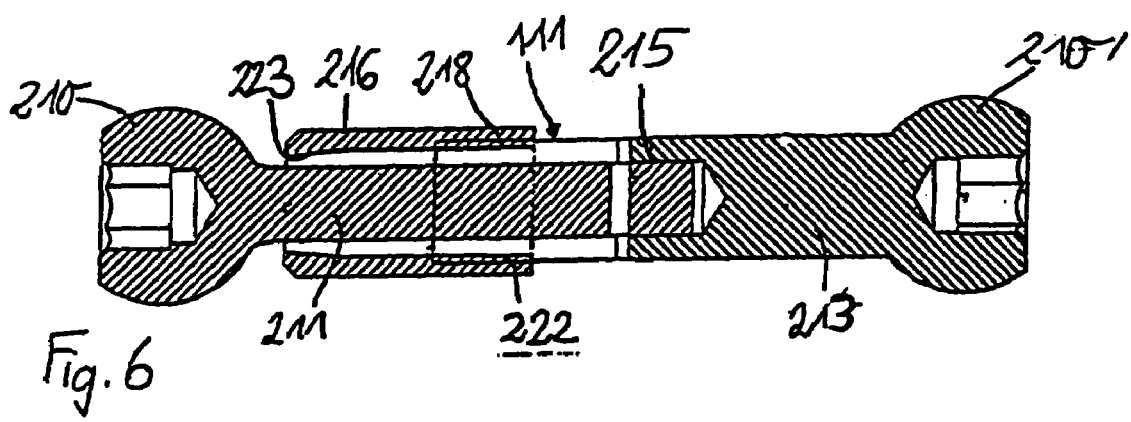
FIG. 6 shows a sectional illustration of the connecting part of FIG. 5 along line A—A.
Figure 7:
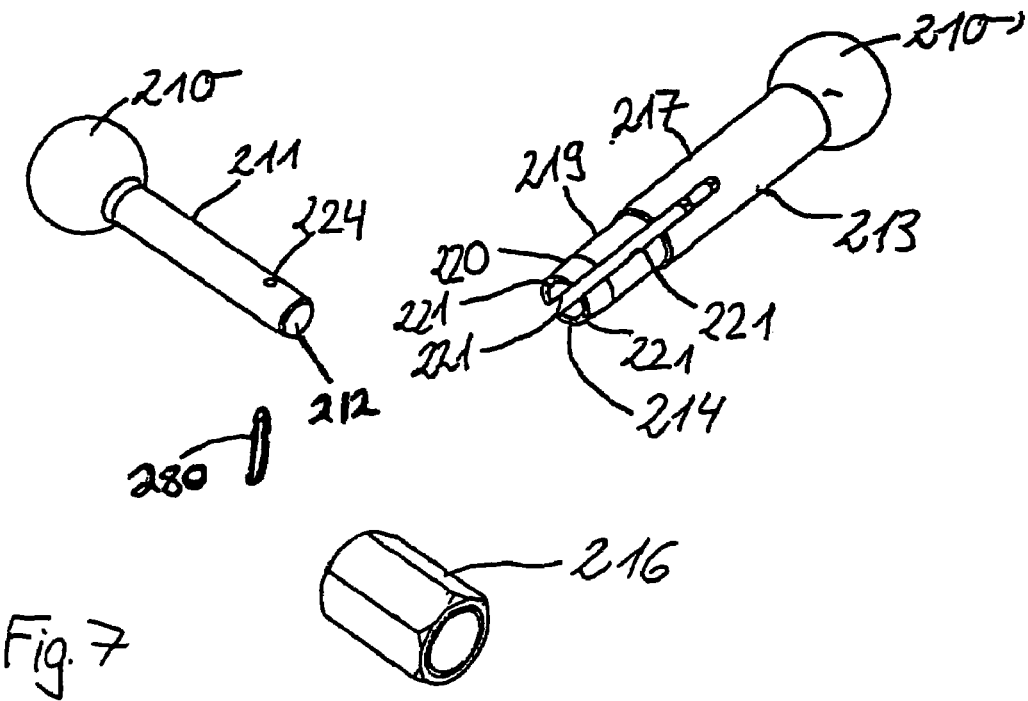
FIG. 7 shows a perspective illustration of the elements of the connecting part of FIG. 5.

The embodiment example shown in FIGS. 5 to 7 differs from the embodiment shown in FIGS. 3 and 4 in the construction of the shank 111, the length of which can to a certain extent be adapted to the distance between the rods. Otherwise this embodiment coincides in all details in respect of the heads, and parts 12, 12', the rods 18, 28 and the nuts 19, 33 with the embodiment according to FIG. 3 and in respect of the mounts 34, the rods 18, 28 and the nuts 19, 33 with the embodiment according to FIG. 4.

As can be seen in particular from FIG. 7, the shank 111 consists of three elements. A first shank part 211 is formed from a pin-shaped section with an open end 212 and connected to one of the heads 210. The diameter of the pin-shaped section is such that the pin-shaped section can be guided through the bore 22 of the mount 12. A second shank part 213 is substantially cylindrically constructed adjacent to the other head 210' and has a coaxial bore 215, extending from the open end 214 to a distance from the head 210' for receiving the first shank part 211. To fix the connection between first and second shank part a nut 216, described in detail later, is provided. The second shank part 213 has adjacent to the head 210' a first cylindrical section 217 with a first outer diameter which is dimensioned in such a way that the shank part 213 can be guided through the bore 22 of the mount 12'. On its end facing away from the head 210' the first cylindrical section 217 has an outer thread 218, indicated in FIGS. 5 and 6. Adjacent to the first cylindrical section 217 the second shank part has a second cylindrical section 219 with an outer diameter which is smaller than that of the first cylindrical section. Adjacent to the second cylindrical section 219 the second shank part has a third section 220, the outer wall of which tapers conically towards the open end 214 at a conical angle. Further provided in the second shank part 213 are at least two, in the embodiment example shown, four longitudinal slots 221, extending from the open end 214 as far as into the first cylindrical section 217 and beyond the region of the outer thread 218, but not as far as the floor of the bore 215. In each case two longitudinal slots 221 are opposite one another. On the second shank part the longitudinal slots form tongues which are to a certain extent elastic, so with the nut 216, described below, a clamping effect on to the inserted first shank part 211 is achievable.

The nut 216 is a spigot nut or tensioning nut. It is constructed as elongated and has adjacent to one of its ends an inner thread 222 which cooperates with the outer thread 218 of the second shank part 213. Adjacent to its opposite end the nut has a section 223, the inner wall of which tapers conically towards the second end of the nut. The length in the direction of the longitudinal axis of the nut and the conical angle correspond to that of the second shank part. The length of the nut is dimensioned in such a way that in the state screwed on to the second shank part 213 the conical region 223 of the nut cooperates with the conical region 220 of the second shank part.

To secure against twisting of the first shank part 211 in respect of the second shank part 213 the first shank part 211 has at a distance from its open end 211 a bore 224, extending crosswise to the shank axis through the pin-shaped section, for receiving a corresponding securing pin 280,. The diameter of the bore corresponds to the diameter of the slots 221 in the crosswise direction. The securing pin to be inserted has a length which is larger than the diameter of the first shank part 211 and a maximum of the size of the core diameter of the nut 216.

In operation first the first shank part 211 is inserted through the bore 22 of the mount 12, shown in FIG. 3, until the head 210 is resting on the floor 23. Then the second shank part 213 is guided through the bore 22 of the other mount 12' until the head 210' is resting on the floor 23. The nut 216 is subsequently screwed by a small amount on to the second shank part 213, so the conical sections of nut and second shank part do not yet cooperate and the first shank part can be inserted. The first shank part 211 is now inserted into the bore 215 of the second shank part 213 until a desired total length of the shaft is produced. However, the nut 216 is still not tightened, so adjustment in length is possible. To secure against twisting, the above-described securing pin 280 is subsequently guided through the longitudinal slots 221 and the bore 224. All the time the nut 216 has not been tightened the length of the shank 111 can still be changed, even with inserted securing pin 280, as the securing pin 280 can be displaced in the slots 221 with the first shank part 211. Thus length adjustment can take place without twisting of the heads 210 or 210'.

Connection of the mounts 12, 12' to the rods 18, 28 then takes place as in the manner described in connection with the embodiment according to FIG. 3.

Finally the nut 216 is tightened. By tightening the nut until the conical sections of nut and second shank part cooperate, the above-described tongues formed in the second shank part 213 by the longitudinal slots 221 are pressed together and thereby clamp the first shank part in a similar way to that with a collect chuck. If it emerges that another length adjustment of the shank 111 is required, only the nut 216 has to be loosened, in order to remove the clamping effect of the tongues. In practice the surgeon first screws the screws into the bone at the desired positions and then places the rods in. The connecting part 10 is usually already pre-mounted before being inserted, i.e. the heads are in the respective mounts and the shank part 211 is inserted into the second shank part 213, so the shank has a predetermined length. The surgeon then places the connecting part between the rods to be connected and adapts the desired length of the shank part as described above. In this way, for example, one rod can also be pulled towards the other.

If the embodiment of the shank 111 shown in FIGS. 5 to 7 is used with the embodiment of the mounts 34 shown in FIG. 4, connection of the shank parts can take place before the heads 210, 210' are connected to the mounts 34, because the shank parts are inserted into the mounts with the head side.

The embodiment shown in FIGS. 5 to 7 can also be applied in the embodiment shown in FIG. 2, wherein one of the heads is then replaced by part 13 and the connecting element then has a monoaxial and a polyaxial connection.

In the above-described embodiment examples the connecting elements are always explained for connecting rods. Two shanks of two screws or one shank of one screw and one rod can also be connected to the connecting element and fixed in the same way.

The invention claimed is:

1. A connecting element for connecting two rod-shaped elements capable of use for bone or vertebra stabilization, the connecting element comprising:
   a first part connectable to a first rod-shaped element;
   a second part connectable to a second rod-shaped element; and
   a connecting part comprising:
      a connecting axis,
      a first section,
      a second section, and
      a securing device that prevents relative twisting between the first section and the second section;
   the first section being displaceable relative to the second section, the first section and the second section being connected in such a way that the length of the connecting part is adjustable in a direction of the connecting axis, wherein
   the first section comprises a substantially pin-shaped first shank part,
   the second section comprises a cylindrical shank part having an open end, an axial bore hole for receiving the first shank part, and longitudinal slots extending inward from the open end forming tongues, and
   the connecting element further comprises a tensioning nut for fixing the first section relative to the second section;
   wherein the tongues clamp the first shank part by the action of the tensioning nut, and
   wherein the first shank part has a bore perpendicular to the connecting axis and the securing comprises a securing pin which extends through at least one of the longitudinal slots and through the bore in the first shank part.

2. The connecting element according to claim 1, wherein the first section is connected to the second section via a clamping device.

3. The connecting element according to claim 1, wherein the first section comprises a substantially pin-shaped first shank part, the second section comprises a second shank part that is structured and arranged as a collect chuck for receiving the first shank part, and wherein the connecting element further comprises a tensioning nut for fixing the first section relative to the second section.

4. The connecting element according to claim 1, wherein the first part is connected to the connecting part in a polyaxially alignable connection and the second part is connected to the connecting part in a monoaxial connection.

5. The connecting element according to claim 1, wherein the first part and the second part both are connected to the connecting part in a polyaxially alignable connection.

6. The connecting element according to claim 1, wherein the connecting part further comprises:
   an end having a head;
   a holding device on the head for receiving, holding and enabling the polyaxial alignment of a rod-shaped element; and
   fixing means for fixing the rod-shaped element in the holding device.

7. The connecting element according to claim 6, wherein the fixing means comprises a nut.

8. The connecting element according to claim 1, wherein the rod-shaped elements are rods.

* * * * *

UNITED STATES PATENT AND TRADEMARK OFFICE
CERTIFICATE OF CORRECTION

PATENT NO.       : 7,195,632 B2
APPLICATION NO.  : 10/470255
DATED            : March 27, 2007
INVENTOR(S)      : Lutz Biedermann et al.

It is certified that error appears in the above-identified patent and that said Letters Patent is hereby corrected as shown below:

On the Title Page

(57) Abstract, line 2      Delete "stabilisation",
Insert --stabilization--

In the Specification

Column 5, line 40      After "280",
Delete ","

Column 6, line 9      Delete "collect",
Insert --collet--

In the Claims

Column 7, line 9, Claim 3      Delete "collect",
Insert --collet--

Signed and Sealed this

Twelfth Day of August, 2008

JON W. DUDAS
*Director of the United States Patent and Trademark Office*